(12) United States Patent
Elliott et al.

(10) Patent No.: US 10,066,914 B2
(45) Date of Patent: Sep. 4, 2018

(54) DISPOSABLE ARROW WIPE WITH CHEMICAL INDICATOR

(71) Applicants:Deane Owen Elliott, Woodbridge, VA (US); Mark Rogers Davidson, Florahome, FL (US)

(72) Inventors: Deane Owen Elliott, Woodbridge, VA (US); Mark Rogers Davidson, Florahome, FL (US)

(*) Notice: Subject to any disclaimer, the term of this patent is extended or adjusted under 35 U.S.C. 154(b) by 0 days.

(21) Appl. No.: 15/694,824

(22) Filed: Sep. 3, 2017

(65) Prior Publication Data

US 2018/0073843 A1 Mar. 15, 2018

Related U.S. Application Data

(63) Continuation-in-part of application No. 15/261,002, filed on Sep. 16, 2016, now Pat. No. 9,759,534.

(51) Int. Cl.
| | |
|---|---|
| *F42B 6/04* | (2006.01) |
| *F42B 12/38* | (2006.01) |
| *F42B 12/40* | (2006.01) |
| *F42B 12/36* | (2006.01) |
| *G01N 21/80* | (2006.01) |
| *F41J 5/14* | (2006.01) |
| *F42B 35/00* | (2006.01) |
| *F41B 5/14* | (2006.01) |
| *G01N 33/84* | (2006.01) |
| *G01N 21/77* | (2006.01) |

(52) U.S. Cl.
CPC .............. *F42B 12/40* (2013.01); *F41B 5/148* (2013.01); *F41J 5/14* (2013.01); *F42B 12/362* (2013.01); *F42B 35/00* (2013.01); *G01N 21/80* (2013.01); *G01N 33/84* (2013.01); *F42B 6/04* (2013.01); *G01N 2021/7759* (2013.01)

(58) Field of Classification Search
CPC .......... F42B 6/04; F42B 12/362; F42B 12/38; G01N 33/726
USPC .................................................. 473/578, 581
See application file for complete search history.

(56) References Cited

U.S. PATENT DOCUMENTS 3,150,875 A * 9/1964 Searles ..................... F42B 6/04
102/334
3,672,351 A * 6/1972 Ubersax ................. A61B 42/10
422/411

(Continued)

FOREIGN PATENT DOCUMENTS

| CN | 202699137 | 1/2013 |
| WO | 2016166592 A1 | 10/2016 |

*Primary Examiner* — Alexander Niconovich
(74) *Attorney, Agent, or Firm* — Patent Law Associates

(57) ABSTRACT

A disposable indicator for use with an arrow or crossbow bolt comprising a substrate and a chemical indicator material capable of detecting and visually indicating chemical properties of a bodily fluid wiped from the arrow by a change in color. Chemical indicating materials may be selected to indicates a variety of bodily fluid chemical properties using pH, enzyme, or detection of other bodily compounds. The indicator provides an immediate indication of the portions of the animal's body through which the arrow or bolt passed, enabling the hunter to determine the type of shot and how best to track the wounded animal. An additional benefit is that the substrate can be used to clean the arrow or bolt in additional to providing a chemical shot indication.

16 Claims, 3 Drawing Sheets

(56) References Cited

U.S. PATENT DOCUMENTS

| | | | | |
|---|---|---|---|---|
| 4,277,069 A * | 7/1981 | Rouse | F42B 12/362 | 473/581 |
| 4,856,792 A * | 8/1989 | Hardison | F42B 12/362 | 362/34 |
| 5,035,435 A * | 7/1991 | Burgeson | F42B 6/04 | 239/34 |
| 5,064,766 A * | 11/1991 | Wardlaw | G01N 33/725 | 422/430 |
| 5,171,528 A * | 12/1992 | Wardlaw | G01N 33/725 | 210/198.3 |
| 6,186,913 B1 * | 2/2001 | Thomas | F42B 12/362 | 473/581 |
| 6,238,310 B1 * | 5/2001 | Morrison | F42B 6/04 | 473/581 |
| 6,641,493 B1 * | 11/2003 | Shifflett | F42B 6/04 | 473/578 |
| 7,426,888 B2 * | 9/2008 | Hunt | F42B 6/04 | 102/513 |
| 7,488,267 B2 * | 2/2009 | Hunt | F42B 6/04 | 473/578 |
| 8,123,636 B1 * | 2/2012 | Temprine | F42B 6/06 | 473/578 |
| 8,152,663 B2 * | 4/2012 | Grundman | F42B 6/04 | 473/578 |
| 8,366,573 B2 * | 2/2013 | Hunt | A63B 65/02 | 473/578 |
| 8,678,961 B2 * | 3/2014 | Wiegand | A61K 35/60 | 43/1 |
| 9,028,348 B2 * | 5/2015 | Lazenby | F42B 6/04 | 473/581 |
| 9,121,678 B1 * | 9/2015 | Kendall | F42B 6/04 | |
| 9,205,164 B2 * | 12/2015 | Sanazaro | F42B 6/08 | |
| 9,335,136 B1 * | 5/2016 | Campbell | F42B 6/04 | |
| 9,759,534 B2 * | 9/2017 | Elliott | F42B 12/362 | |
| 2006/0044792 A1 * | 3/2006 | Dallas | G01J 3/10 | 362/184 |
| 2008/0014151 A1 * | 1/2008 | Okuno-Jones | A61K 8/02 | 424/10.3 |
| 2013/0087298 A1 * | 4/2013 | Phillips | D21H 27/002 | 162/148 |
| 2016/0106880 A1 * | 4/2016 | Coomber | A61K 49/006 | 424/9.1 |

* cited by examiner

DISPOSABLE ARROW WIPE WITH CHEMICAL INDICATOR

CROSS-REFERENCE TO RELATED APPLICATIONS

This application is a continuation-in-part of U.S. application Ser. No. 15/261,002, filed Sep. 9, 2016.

BACKGROUND OF THE INVENTION

The present invention relates generally to archery hunting using an arrow or cross bow bolt and, more particularly, to a chemical indicator enabling a hunter to determine whether a game animal was hit by the arrow or bolt.

In archery hunting, shot placement is very critical to ensuring a quick and humane kill. Archers practice for hours to make sure they make ethical shots when hunting. The most desired shot by an archery hunter is referred to as a "double lung" shot where the arrow or bolt passes through both lungs of an animal standing broadside to the hunter. With today's compound bow and crossbow technology, it is very difficult to determine where the arrow or bolt has gone once it leaves the bow or crossbow due to the speed that the projectile is traveling. Many crossbow bolts are traveling at velocities approaching 400 feet per second. The projectile velocity also means that the arrow or bolt frequently passes completely though the animal.

Archery hunters are generally physically close to their prey when taking a shot, generally forty yards or less. Deer may often sense a hunter's presence and be additionally alert. Deer often hear the release of the arrow from the bow before the arrow reaches them which allows them to initiate movement. This movement can affect the impact point of the arrow or bolt. A broadside shot when aimed can quickly become a quartering shot in which the arrow impacts the animal at an angle, either from the rear to the front or from the front to the rear, which may not be as lethal as the desired transverse double lung shot. Such quartering shots are more likely to result in an arrow passing at least partially through the animal's digestive tract or other parts of the animal's anatomy.

Given the difficulty of observing the arrow during its flight to the target, hunters usually seek the arrow afterward in order to examine it for indications of the shot. An arrow having hit its target will be covered in blood and other internal fluids from having passed through the target animal.

Animal blood is generally neutral, having a pH in the range of 7.35 to 7.45. Shots passing through the animal's lungs would be exposed to primarily to blood. Digestive fluids in the animal's gut are highly acidic, generally having a pH ranging from 1 to 4.5. A shot passing thorough the animal's gut is likely to be exposed to digestive fluids in addition to blood. Shots passing through other organs may be exposed to other bodily fluids having chemically distinguishable characteristics, such as pH, enzymes, and the like. A variety of chemical compounds are known to exhibit color changes upon contact with fluids of various pH, specifically including color changes when contacting acidic fluids. Some compounds react only to pH values within small ranges thereby enabling relatively precise identification of the pH of the fluids.

It would be advantageous to provide a disposable indicator capable of detecting and indicating chemical properties of a bodily fluid by a visible change in color that would provide an immediate indication of the portions of the animal's body through which the arrow or bolt passed that would permit the hunter to determine how the animal should be tracked. If an indicator shows that the animal has been hit in the stomach region (a gut shot), it is best for the hunter to back away and allow the animal to lay down and die rather than to pursue it immediately. When hunting deer, an animal that has been gut shot is often left to lay overnight if weather conditions allow so as not to jump it from its bedded location which can easily cause the wounded animal to travel as much as a mile before bedding down again. Conversely, if the indicator shows a clean, non-gut shot, has occurred, the hunter can begin tracking the animal in a normal practice of waiting a short time (one-half hour). Configuring the indicator in the form of a disposable wipe enables the indicator to be used with any arrow or bolt simply by wiping once it is recovered. An additional benefit is that the wipe can be used to clean the arrow in additional to providing a chemical shot indication.

SUMMARY OF THE INVENTION

Accordingly, the present invention, in any of the embodiments described herein, may provide one or more of the following advantages:

It is an object of the present invention to provide a wipe for an arrow comprising an indicator that will chemically indicate the pH or other chemical characteristics of the fluids that have contacted the arrow as it passed through the target animal.

It is a further object of the present invention to provide a wipe for an arrow or bolt comprising an absorptive neutral carrier substrate on which a chemical indicator material is applied. The chemical indicator material may be selected to react when exposed to fluids having a specific pH or range of pH values. A plurality of indicator materials may be applied to enable indication of exposure to different types of bodily fluids using different types of chemical reactions, such as blood, stomach acids, bile, or other enzymes.

It is a further object of the present invention to provide a chemically indicating wipe for an arrow or bolt having that may also be treated with non-chemically reactive substances to enable the wipe to be used to clean the arrow or bolt for reuse.

It is a still further object of the present invention to provide a wipe for an arrow or bolt that is chemically reactive to indicate the acidity of the bodily fluids to which the arrow or bolt has been exposed that is inexpensive of manufacture, carefree of maintenance, and simple and effective to use.

These and other objects of the present invention are fulfilled by a disposable wipe for an arrow or bolt comprising a substrate in the form of a wipe or cloth and an indicator applied to the substrate that will chemically react with fluids to which they are exposed, such as when wiping fluids from an arrow or bolt that has passed through an animal. A plurality of chemical indicators may be applied to the substrate enabling reactive indication of numerous bodily fluids to which the arrow or bolt might have been exposed. The substrate may also be treated with a non-reactive material enabling the wipe to effectively clean the arrow or bolt for reuse

BRIEF DESCRIPTION OF THE DRAWINGS

The advantages of this invention will be apparent upon consideration of the following detailed disclosure of the invention, especially when taken in conjunction with the accompanying drawings wherein.

DESCRIPTION OF THE PREFERRED EMBODIMENT(S)

Many of the fastening, connection, processes and other means and components utilized in this invention are widely known and used in the field of the invention described, and their exact nature or type is not necessary for an understanding and use of the invention by a person skilled in the art, and they will not therefore be discussed in significant detail. The various components shown or described herein for any specific application of this invention can be varied or altered as anticipated by this invention and the practice of a specific application of any element may already be widely known or used in the art by persons skilled in the art and each will likewise not therefore be discussed in significant detail. When referring to the figures, like parts are numbered the same in all of the figures. As used herein, the term arrow also applies to crossbow bolts.

Figure 2:
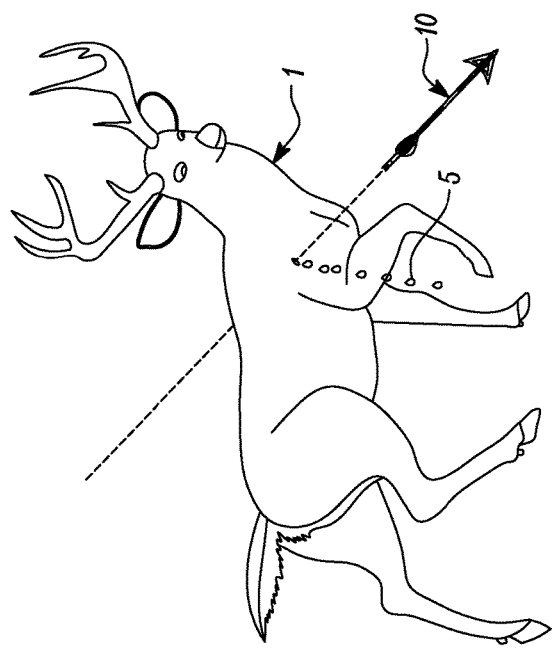
FIG. 2 illustrates a target animal having been struck in the gut by an arrow.
Figure 1:
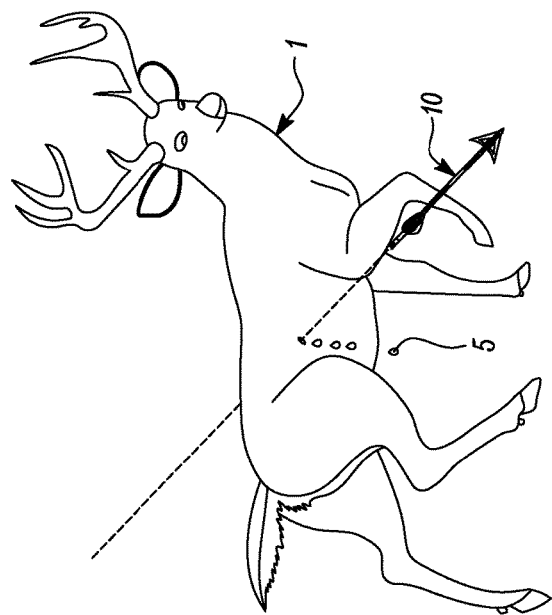
FIG. 1 illustrates a target animal having been ideally struck by an arrow.

Referring to FIGS. 1 and 2 there is shown a game animal 1, such as a deer, that is frequently hunted by archers using bows or crossbows. In FIG. 1, a traditional crossbow bolt or arrow 10 is shown having struck and penetrated the animal 1 in the most desired shot by an archery hunter which is referred to as a "double lung" or "kill" shot where the arrow or bolt 10 passes through both lungs of an animal standing broadside to the hunter. In FIG. 2, the animal 1 is shown having been shot in the gut wherein the arrow 10 passes predominately through the portion of the animal where the digestive tract is internally located. Such shots are generally less lethal and may allow the animal to flee from the location. In either shot, internal bodily fluids are deposited on the arrow 10 as it passes through the animal and typically remain on the arrow thereafter.

Figure 3:
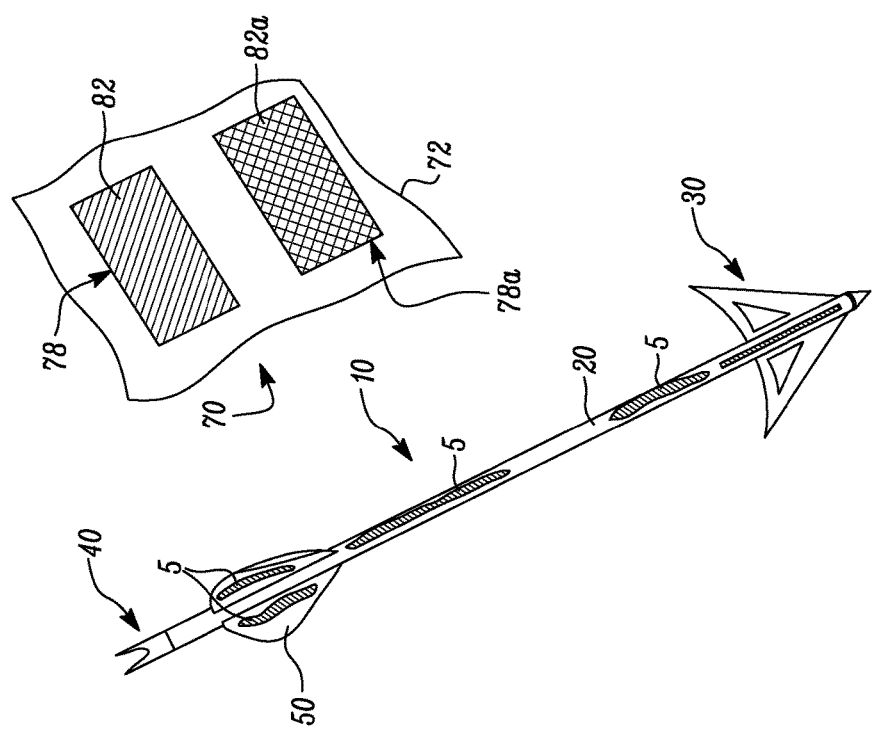
FIG. 3 illustrates a conventional arrow that has been retrieved following striking of a target animal and a first embodiment of the present invention.
Figure 4:
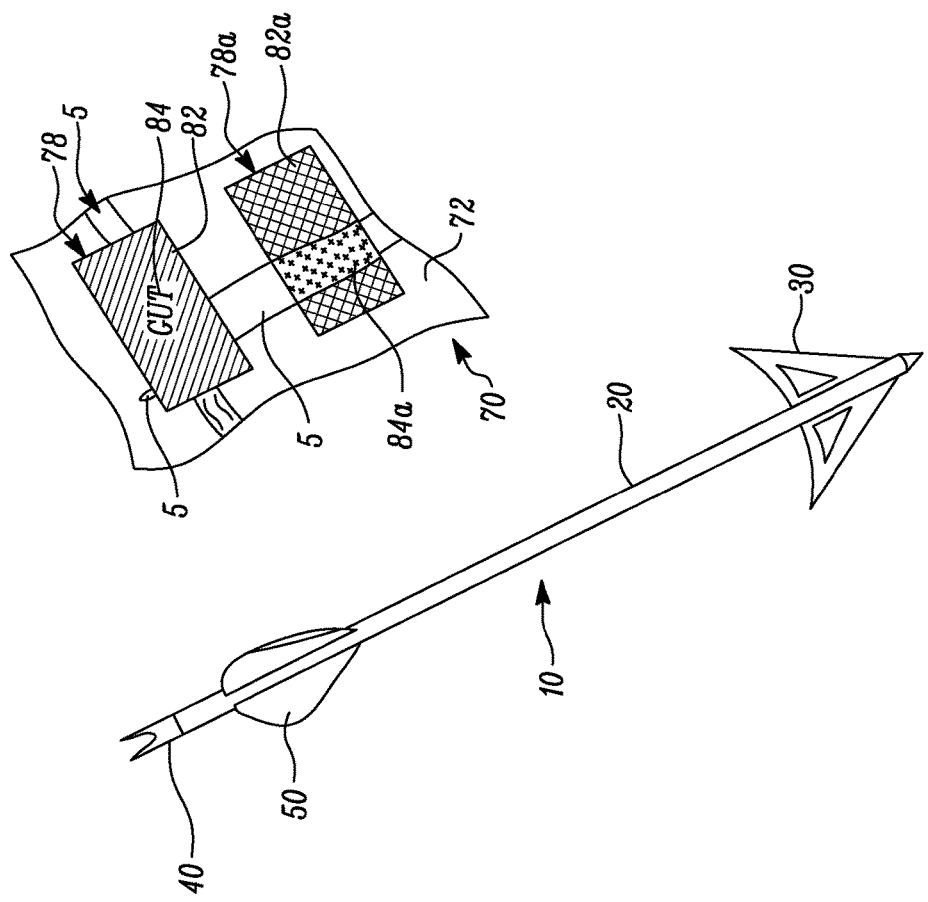
FIG. 4 illustrates the arrow of FIG. 3 wherein the invention has been used to clean the arrow of bodily fluids from the target animal.

Referring to FIGS. 3 and 4, a conventional arrow or bolt 10 is illustrated comprising an elongate shaft 20 having a broadhead tip 30 at one end and a traditional nock 40 for engaging the string of a crossbow or bow at the opposite end. Fletchings or vanes 50 may be attached to the shaft 20, typically proximate to the trailing end where the nock 40 is located, to guide the arrow 10 in flight.

In FIG. 3, the arrow or bolt 10 is shown having passed through the animal 1 where it interacts with bodily fluids 5, some of which are transferred to the arrow. In an ideal shot (FIG. 1), the arrow 10 passes through the animal's chest and interacts with the heart and/or lungs which contain mainly blood. Animal blood is generally understood to have a generally neutral acidity with a pH in the range of 7.35 to 7.45. A pH of 7 is considered neutral. The gut shot illustrated in FIG. 2 passes wholly or partially through the animal's digestive tract where it is likely to be exposed to digestive fluids in addition to blood. The stomach pH of herbivores is typically around 4.5 (slightly acidic) while the stomach pH of carnivores and omnivores is typically between 1 and 3. Testing the bodily fluids 5 on the arrow 10 for pH provides a method to distinguish a kill shot from a gut shot.

An indicator 70 is provided comprising a substrate 72 and at least one chemical indicator material 78 applied thereto. The chemical indicator material 78 may be applied during a production process so that the end user need only wipe an arrow 10 with the indicator 70, or the chemical indicator material 78 may be applied by a user to the substrate 72 after the user has located the arrow and is preparing to wipe the outer surface. It is also envisioned that a user could apply the chemical indicator material 78 directly to the arrow and then wipe with the substrate 72 to observe the visual color change. It is preferred to apply the chemical indicator material 78 to the substrate 72 prior to any interaction with potential bodily fluids 5 of the animal so that the color change may be witnessed against the backdrop of the substrate 72, preferably rendered in white for maximum color contrast.

The substrate 72 may be in the form of a flexible wipe made of woven, non-woven, or any other fabric material that exhibits generally neutral characteristics. The substrate 72 may require treatment prior to use to assure it has a neutral or slightly basic pH that will not react with the chemical indicator material 78 prior to use arrow. Many cellulose-based materials are known to be slightly acidic in their readily available form. Pre-treating cellulose-based substrates with sodium bicarbonate (baking soda) has proven an effective way to neutralize substrates prior to application of the chemical indicating material 78.

The chemical indicator material 78 is selected to chemically react with the bodily fluids 5 to which it is exposed and to provide a visual color change from a first visually perceived color 82 to a second visually perceived color 84 in the event that such bodily fluids 5 exhibit chemical properties for which the indicator was selected. In one embodiment, the indicator material 78 reacts to the acidity (pH) of the fluid, the color change being from a first color 82 representing neutral acidity and a second color 84 indicating exposure to acidic solutions which is indicative of a shot that has pierced the animal's gut.

The chemical indicator material 78 may be a chemical indicating dye, referred to as a halochromic chemical compound, which undergoes color changes when exposed to varying pH levels or changes. One such indicating dye phenaphthazine yellow, also known as Nitrazine Yellow, which is blue in color under neutral conditions and changes to yellow/tan when exposed to acidic solutions. Another indicating dye is bromothymol sulfone phthalein, also known as bromothymol blue, which is also normally blue in color, but changes color to yellow when exposed to acidic fluids. These color changes are preferred as they provide contrast to the red color of the blood that is likely to be present on the indicator as well. Numerous other chemicals are known to exhibit color changes when exposed to acidic solutions and offer the ability to refine the range(s) of pH causing color change and even the resultant color, including lacmoids and methyl red. Other indicator dyes may also be used, including a universal indicator dye that exhibits color changes across the entire acid-base pH spectrum.

The chemical indicator material 78 may be selected based on the intended prey of the hunter. The stomach pH of herbivores is typically around 4.5 (slightly acidic) while the stomach pH of carnivores and omnivores is typically between 1 and 3. By selecting a halochromic chemical compound that undergoes color transition during the anticipated pH range, the accuracy of the indicator 70 can be improved and optimized for the intended prey.

It may also be desirable to confirm that the arrow 10 struck the animal 1. Hunting during wet conditions or when the arrow travels a significant distance in leaves or earth may wipe the animal's bodily fluids 5 from the arrow or ground moisture may provide the appearance that the arrow pierced the animal when in fact it did not. The use of chemical luminescence (materials that react with enzymes and iron in hemoglobin) allows even minute traces of blood to be visually indicated. Such materials are commonly identified as Blue Star, Luminol, HemaScein, and Flora-Scene, but all involve materials that chemically react with blood and fluoresce to indicate the presence of blood.

Multiple indicator materials 78, 78a may be provided on the substrate 72 to indicate the presence of different bodily fluids and thus inform a hunter of the type of shot using a single indicator 70 exposed to the fluids present on the arrow. By choosing a first indicator material 78 that is reactive to the pH of the bodily fluid 5 by displaying a second color 84 and a second indicator 78a that is reactive to the presence of blood by displaying a second color 84a, the indicator 70 is capable of confirming both that the arrow pierced the animal and whether the arrow pierced the animal's digestive tract.

Upon inspection after a broadside double-lung shot, a hunter noting the unchanged color of the indicator 70 can deduce that the shot was not a gut shot and the animal will not travel far from the location at which it was shot before succumbing to the wound. A hunter retrieving the arrow and observing that the indicator 70 has changed to the second color can deduce that the shot was a gut shot and that the animal may travel further from the location at which it was shot before succumbing to the wound, especially if the hunter attempts to locate the fallen animal. Deer have been known to run as much as a mile before succumbing to a gut shot.

In FIG. 4, the arrow 10 has been wiped clean with an indicator 70 which comprises a substrate 72 with chemical indicator materials 78, 78a applied beforehand. The most straightforward approach is to apply the chemical indicator materials 78, 78a in designated positions on the substrate 72 and make that known to the user by easily understood means. The chemical indicator materials 78, 78a will appear as the first color 82, 82a, which may be the same or may differ. Upon exposure to the bodily fluids 5 wiped from the arrow 10, the chemical indicating materials 78, 78a may display a second color 84, 84a indicating the presence of a specific bodily fluid based on chemical reaction. The second color will generally be defined by the way the fluids are dispersed on the substrate as the arrow is wiped clean.

The chemical indicating materials 78, 78a may be configured so that the second color 84, 84a displayed upon reaction with the specific bodily fluids provides indicia of the type of chemical indication for convenience to the hunter. As is illustrated, the chemical indicating material 78 reacting with digestive tract fluids (acids) by indicating a "gut" shot rendered in the second color 84 against the first color 82 background. A similar approach could be used with chemical indicator materials reacting with blood. Communicating results to the hunter simply requires a color change from a first color to a visually distinguishable second color. In the event no color change is exhibited, the hunter may conclude that the arrow missed the target animal and forego searching for the animal.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

We claim:

1. A method for confirming that an arrow has struck an animal and indicating where the arrow penetrated the animal comprising the steps of:
   providing a wiping material substrate;
   providing an indicator material;
   applying the indicator material to the wiping material substrate;
   shooting an arrow toward the animal;
   retrieving the arrow and wiping the arrow with the wiping material substrate having the indicator material applied thereto; and
   observing the indicator material on the wiping material substrate, the indicator material being visually perceived as a first color when applied to the wiping material substrate, the indicator material being visually perceived as a second color different from the first color when subjected to and chemically reacting with a specific bodily fluid from the animal wiped from the arrow, the indicator material otherwise being visually perceived as the first color.

2. The method of claim 1, further comprising the step of:
   selecting the indicator material to react with the specific bodily fluid to indicate a chemical property thereof, the chemical property being indicative of a portion of the animal through which the arrow passed.

3. The method of claim 2, wherein a plurality of indicator materials may be applied to the wiping material substrate, the plurality of indicator materials selected to indicate interaction with a plurality of specific bodily fluids, including at least blood, stomach acids, bile, enzymes, and digestive tract fluids.

4. The method of claim 2, further comprising the steps of:
   determining based on the indicator material selected and the perceived second color a time necessary for the animal to most likely succumb to wound; and
   initiating a search for the animal after it has most likely succumbed to the wound and is unable to further evade the search.

5. The method of claim 2, wherein the indicator material reacts with the specific bodily fluid to indicate a pH value thereof.

6. The method of claim 5, wherein the indicator material is a halochromic chemical compound.

7. The method of claim 6, wherein the halochromic chemical compound is selected based on a finite range of pH values suggestive of an internal source of the bodily fluid.

8. The method of claim 6, wherein the indicating material is a halochromic chemical compound selected from the group comprising nitrazine yellow, lacmoids, methyl red, and bromothymol blue.

9. A method for confirming that an arrow has struck an animal and indicating where the arrow penetrated the animal comprising the steps of:
   providing a wiping material substrate;
   providing an indicator material;
   shooting an arrow toward the animal;
   retrieving the arrow;
   applying the indicator material to the arrow;
   wiping the arrow with the wiping material substrate; and
   observing the indicator material on the wiping material substrate, the indicator material being visually perceived as a first color when applied to the arrow, the indicator material being visually perceived as a second color different from the first color when subjected to and chemically reacting with a specific bodily fluid from the animal wiped from the arrow, the indicator material otherwise being visually perceived as the first color.

10. The method of claim 9, further comprising the step of:
selecting the indicator material to react with the specific bodily fluid to indicate a chemical property thereof, the chemical property being indicative of a portion of the animal through which the arrow passed.

11. The method of claim 10, further comprising the steps of:
determining based on the indicator material selected and the perceived second color a time necessary for the animal to most likely succumb to wound; and
initiating a search for the animal after it has most likely succumbed to the wound and is unable to further evade the search.

12. The method of claim 10, wherein the indicator material reacts with the specific bodily fluid to indicate a pH value thereof.

13. The method of claim 12, wherein the indicator material is a halochromic chemical compound.

14. The method of claim 13, wherein the halochromic chemical compound is selected based on a finite range of pH values suggestive of an internal source of the bodily fluid.

15. The method of claim 14, wherein the indicating material is a halochromic chemical compound selected from the group comprising nitrazine yellow, lacmoids, methyl red, and bromothymol blue.

16. The method of claim 10, wherein a plurality of indicator materials may be applied to the wiping material substrate, the plurality of indicator materials selected to indicate interaction with a plurality of specific bodily fluids, including at least blood, stomach acids, bile, enzymes, and digestive tract fluids.

* * * * *